United States Patent [19]

MacDonald

[11] 4,018,748

[45] * Apr. 19, 1977

[54] POLYAMIDES CONTAINING 1,2,5-OXADIAZOLE-3,4-DICARBONYL GROUPS

[75] Inventor: Robert N. MacDonald, Wilmington, Del.

[73] Assignee: E. I. Du Pont de Nemours and Company, Wilmington, Del.

[*] Notice: The portion of the term of this patent subsequent to May 23, 1989, has been disclaimed.

[22] Filed: Jan. 24, 1973

[21] Appl. No.: 326,175

[52] U.S. Cl. .................. 260/78 R; 260/33.8 R; 260/47 CZ

[51] Int. Cl.² ........................ C08G 69/32

[58] Field of Search .................. 260/78 R

[56] References Cited

UNITED STATES PATENTS 2,130,948  9/1938  Carothers .............. 260/78 R
3,664,986  5/1972  MacDonald ............ 260/78 R Primary Examiner—Harold D. Anderson

[57] ABSTRACT

Polyamides of the formula

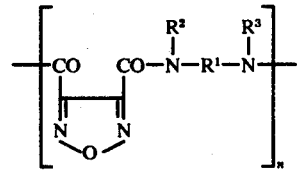

wherein $R^1$ is an alkylene group of 2–12 carbon atoms or, any arylene or a bisarylene group of 6–18 carbon atoms, and $R^2$ and $R^3$ are hydrogen, alkyl of up to 6 carbon atoms or, when $R^1$ is an alkylene group, $R^2$ and $R^3$ can additionally be alkylene of 2 to 12 carbon atoms.

3 Claims, No Drawings

POLYAMIDES CONTAINING 1,2,5-OXADIAZOLE-3,4-DICARBONYL GROUPS

BACKGROUND OF THE INVENTION

1. Field of the Invention

This invention relates to novel polyamides which can be formed into films and fibers.

2. The Prior Art

MacDonald, U.S. Pat. No. 3,664,986 has described polymers containing 1,2,5-thiodiazole-3,4-dicarbonyl groups which can be formed into films and fibers.

DESCRIPTION OF THE INVENTION

This invention comprises novel polyamides having the formula wherein $R^1$ is alkylene of 2 to 12 carbon atoms or an arylene or a bisarylene group of 6–18 carbon atoms and $R^2$ and $R^3$ are hydrogen, alkyl of up to 6 carbon atoms or when $R^1$ is an alkylene group, $R^2$ and $R^3$ jointly can be alkylene of 2 to 12 carbon atoms; and $n$ is the degree of polymerization, and having an inherent viscosity of from 0.1 to 10 measured in 0.1% solution in chloroform at 25° C.

Preferred embodiments can be represented by the formula wherein $R^4$, $R^5$, $R^6$ and $R^7$ are each hydrogen or an alkyl group of up to four carbon atoms. Particularly preferred compounds are derived from piperazine and trans-2,5-dimethylpiperazine.

Examples of other diamines which can be reacted with 1,2,5-oxadiazole-3,4-dicarbonyl chloride to give useful products are 1,6-hexamethylene diamine, N,N'-diethyl-1,6-hexamethylene diamine; 1,12-dodecamethylene diamine, 1,6-diamino-3,3-dimethylhexane, N,N'-diisobutyl-1,6-diamine-2-ethylhexane, trans-2,3,5,6-tetramethylpiperazine, ethylenediamine, the arylenediamines, including o-, m- and p-phenylenediamines, 1,5-diaminonaphthalene, 2,4- and 2,6-diaminotoluene, 2,6-dichloro-p-phenylenediamine, benzidine and 2,5,2',5'-tetrachlorobenzidine; and the bis-arylenediamines of the formula $$H-N-R^1-N-H$$
$$\;\;\;\;|\;\;\;\;\;\;\;\;|$$
$$\;\;\;R^2\;\;\;\;\;R^3$$

in which $R^1$ is in which $x$ may be O, S, alkylene of up to 6 carbon atoms or haloalkylene of up to 6 carbon atoms and the phenyl rings may be substituted with up to 4 halogens, particularly fluorine, chlorine or bromine, including 4,4'-diaminodiphenyl ether, 4,4'-diaminodiphenyl sulfide, 4,4'-diaminodiphenylene-bis-(trifluoromethyl)methane, 2,2'-diaminodiphenylmethane, 2,2'-diamino-3,5,6-trichlorodiphenylmethane, and the like.

The degree of polymerization (n) is preferably at least 4.

The reactions can be accomplished readily by conventional interfacial polymerization techniques, which for convenience can be conducted at or in the vicinity of ambient temperature.

The product polyamides are suitable for spinning from the melt or from solution into fibers or can be fabricated into useful films and the like by techniques well known in the art.

This invention is further illustrated by the following specific embodiment, which should not, however, be construed as limiting.

EXAMPLE

A. Preparation of 1,2,5-oxadiazole-3,4-dicarbonyl chloride

In a glass reactor under a blanket of nitrogen was placed 120 ml of thionyl chloride and 15.8 g of 1,2,5-oxadiazole-3,4-dicarboxylic acid (Grundmann, Ber. 97 (2), 575–8, 1964). The mixture was heated to reflux and 0.5 ml of dimethylformamide was added. In the ensuing vigorous reaction HCl and $SO_2$ were given off. Refluxing was continued for about 1 hour until all the free acid was dissolved. Excess thionyl chloride was removed at 50° C under vacuum and the residue distilled at 35° C/0.5 mm. Two redistillations gave 13.5 g of 1,2,5-oxadiazole-3,4-dicarbonyl chloride in the form of a colorless liquid boiling at 62°–64° C/9 mm. Infrared absorption at 1760 $cm^{-1}$ (C=O) and at 1525 $cm^{-1}$ and 1440 $cm^{-1}$ (—C=N) was consistent with the proposed structure.

Anal. Calcd. for $C_4O_3N_2Cl_2$: C, 24.7; N, 14.4; Cl, 36.40; H, 0.0; Found: C, 25.5; N, 13.21; Cl, 36.75; H, 0.9.

B. Polyamide from trans-2,5-dimethylpiperazine and 1,2,5-oxadiazole-3,4-dicarbonyl chloride B. Polyamide from trans-2,5-dimethylpiperazine and 1,2,5-oxadiazole-3,4-dicarbonyl chloride

| | -continued |
|---|---|
| B. | Polyamide from trans-2,5-dimethylpiperazine and 1,2,5-oxadiazole-3,4-dicarbonyl chloride |

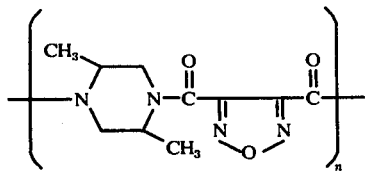

In a glass jacketed blender a mixture of 6.46 g (0.0567 mole) of trans-2,5-dimethylpiperazine, 4.00 g (0.1 mole) of sodium hydroxide in 50 ml of aqueous solution, 120 ml of water, and 30 ml of alcohol-free chloroform was stirred rapidly at 9° C as a solution of 9.75 g (0.05 mole) 1,2,5-oxadiazole-3,4-dicarbonyl chloride in 35 ml of anhydrous, alcohol-free chloroform was added all at once. The temperature rose immediately to 27° C and dropped at 13° C as stirring was continued for 5 minutes. The system was poured into 2 l. of acetone to precipitate sodium chloride which was filtered off. Evaporation of some of the filtrate gave 0.8 g of water-insoluble polyamide. It was washed with water and dried at 80° C/5 mm overnight. Its inherent viscosity was found to be 0.54 (0.1% in chloroform at 25° C) and its stick temperature on a gradient bar was 235° C. No glass transition could be observed. Its thermogravimetric air weight losses were 5% at 253° C and 50% at 376° C.

Anal. Calcd. for $C_{10}H_{12}N_4H_3$: C, 50.83; H, 5.08; N, 23.72; Found: C, 50.37; H, 5.36; N, 22.62; 50.00 5.22 22.51

Infrared absorption was consistent with the above structure: 3.35 $\mu$ and 3.40 $\mu$ for saturated C—H; 6.08 $\mu$ for carbonyl; 6.43 $\mu$ and 6.65 $\mu$ for ring C=N; and 7.22 $\mu$ for C—$CH_3$.

Water absorption of a tough film cast from chloroform was found to be 3%, a property favorable to retention of fiber properties in laundry cycles.

Since obvious modifications and equivalents in the invention will be evident to those skilled in the art, I propose to be bound solely by the appended claims.

The embodiments of the invention in which an exclusive property or privilege is claimed are defined as follows:

1. A polyamide consisting of repeating units of the formula

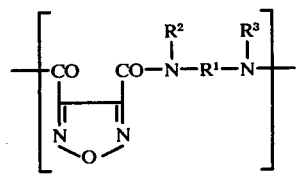

wherein $R^1$ is alkylene of 2 to 12 carbon atoms or an arylene or a bis-arylene group of 6–18 carbon atoms and $R^2$ and $R^3$ are hydrogen, alkyl of up to 6 carbon atoms or when $R^1$ is an alkylene group and $R^2$ and $R^3$ jointly can be alkylene of 2 to 12 carbon atoms, said polyamide having an inherent viscosity measured at 0.1% concentration in chloroform at 25° C between 0.1 and 10.

2. A polyamide consisting of repeating units of the formula

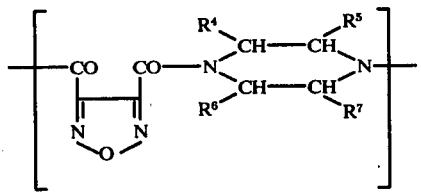

wherein $R^4$, $R^5$ and $R^6$ and $R^7$ are each hydrogen or alkyl of up to 4 carbon atoms, said polyamide having an inherent viscosity measured at 0.1% concentration in chloroform at 25° C of from 0.1 to 10.

3. The polyamide of claim 2 wherein $R^4$ and $R^7$ are methyl and $R^5$ and $R^6$ are hydrogen.

* * * * *